(12) United States Patent
Zhang et al.

(10) Patent No.: US 11,129,400 B2
(45) Date of Patent: Sep. 28, 2021

(54) METHOD OF ECOLOGICAL UTILIZATION OF SILVER CARP

(71) Applicants: Junjie Zhang, Lianyungang (CN); Gongcheng Wang, Lianyungang (CN); Yingdong Zhang, Lianyungang (CN); Rui Duan, Lianyungang (CN); Feiwen Mao, Albertson, NY (US); Boyan Zhang, Lianyungang (CN)

(72) Inventors: Junjie Zhang, Lianyungang (CN); Gongcheng Wang, Lianyungang (CN); Yingdong Zhang, Lianyungang (CN); Rui Duan, Lianyungang (CN); Feiwen Mao, Albertson, NY (US); Boyan Zhang, Lianyungang (CN)

( * ) Notice: Subject to any disclaimer, the term of this patent is extended or adjusted under 35 U.S.C. 154(b) by 363 days.

(21) Appl. No.: 15/995,610

(22) Filed: Jun. 1, 2018

(65) Prior Publication Data

US 2019/0090521 A1    Mar. 28, 2019

(30) Foreign Application Priority Data

Sep. 27, 2017    (CN) .......................... 201710891591.X

(51) Int. Cl.
*A23L 17/00*    (2016.01)
*A22C 25/14*    (2006.01)
(Continued)

(52) U.S. Cl.
CPC .............. *A23L 17/65* (2016.08); *A22C 25/02* (2013.01); *A22C 25/142* (2013.01); *A22C 25/145* (2013.01); *A22C 25/18* (2013.01); *A22C 25/20* (2013.01); *A23B 4/005* (2013.01); *A23B 4/0056* (2013.01); *A23J 1/04* (2013.01); (Continued)

(58) Field of Classification Search
None
See application file for complete search history.

(56) References Cited

PUBLICATIONS

Liu, Yongle; et al; "Characterization of structural and functional properties of fish protein hydrolysates from surimi processing by-products" Food Chemistry, 151, 459-465, 2014 (Year: 2014).*

(Continued)

*Primary Examiner* — David W Berke-Schlessel
(74) *Attorney, Agent, or Firm* — The Roy Gross Law Firm, LLC; Roy Gross

(57) ABSTRACT

A method for ecological utilization of silver carp, including the pretreatment of silver carp and the process of making canned fish surimi. The fish meat of silver carp is processed canned surimi. The fish heads and bones are heated and undergo enzymatic hydrolysis by enzymes, and the residues of the filtration are prepared for fish bone powder. A filtration membrane is used to reduce the volume of the filtrate to 50% of fish surimi and then the filtrate is frozen to ice. The frozen part can be added to fish surimi. The transparent part from membrane filtration was used to produce protein powder or ingredients for beverages. Fish offal can be used to produce protein liquid fertilizer. Fish scales and skins can be used to produce collagen. The method adopts ecological utilization, which makes the silver carp meat used effectively, including its processed wastes. The method is a closed cycle process such that that no pollutants or wastes are discharged during the process.

14 Claims, 1 Drawing Sheet

(51) Int. Cl.

| | |
|---|---|
| A22C 25/02 | (2006.01) |
| A22C 25/18 | (2006.01) |
| A22C 25/20 | (2006.01) |
| A23L 17/10 | (2016.01) |
| A23J 1/04 | (2006.01) |
| A23L 2/66 | (2006.01) |
| A23L 33/18 | (2016.01) |
| A23B 4/005 | (2006.01) |
| A23L 3/10 | (2006.01) |
| C05F 1/00 | (2006.01) |
| C07K 14/78 | (2006.01) |
| A23J 1/10 | (2006.01) |
| A23J 3/34 | (2006.01) |

(52) U.S. Cl.
CPC ............... *A23J 1/10* (2013.01); *A23J 3/341* (2013.01); *A23L 2/66* (2013.01); *A23L 3/10* (2013.01); *A23L 17/10* (2016.08); *A23L 17/70* (2016.08); *A23L 33/18* (2016.08); *C05F 1/002* (2013.01); *C07K 14/78* (2013.01); *A23V 2002/00* (2013.01); *Y02A 40/20* (2018.01)

(56) References Cited

PUBLICATIONS

Martin-Sanchez; et al; "Alternatives for Efficient and Sustainable Production of Surimi: A Review" Comprehensive Reviews in Food Science and Food Safety, 8; 359-374, 2009 (Year: 2009).*

* cited by examiner

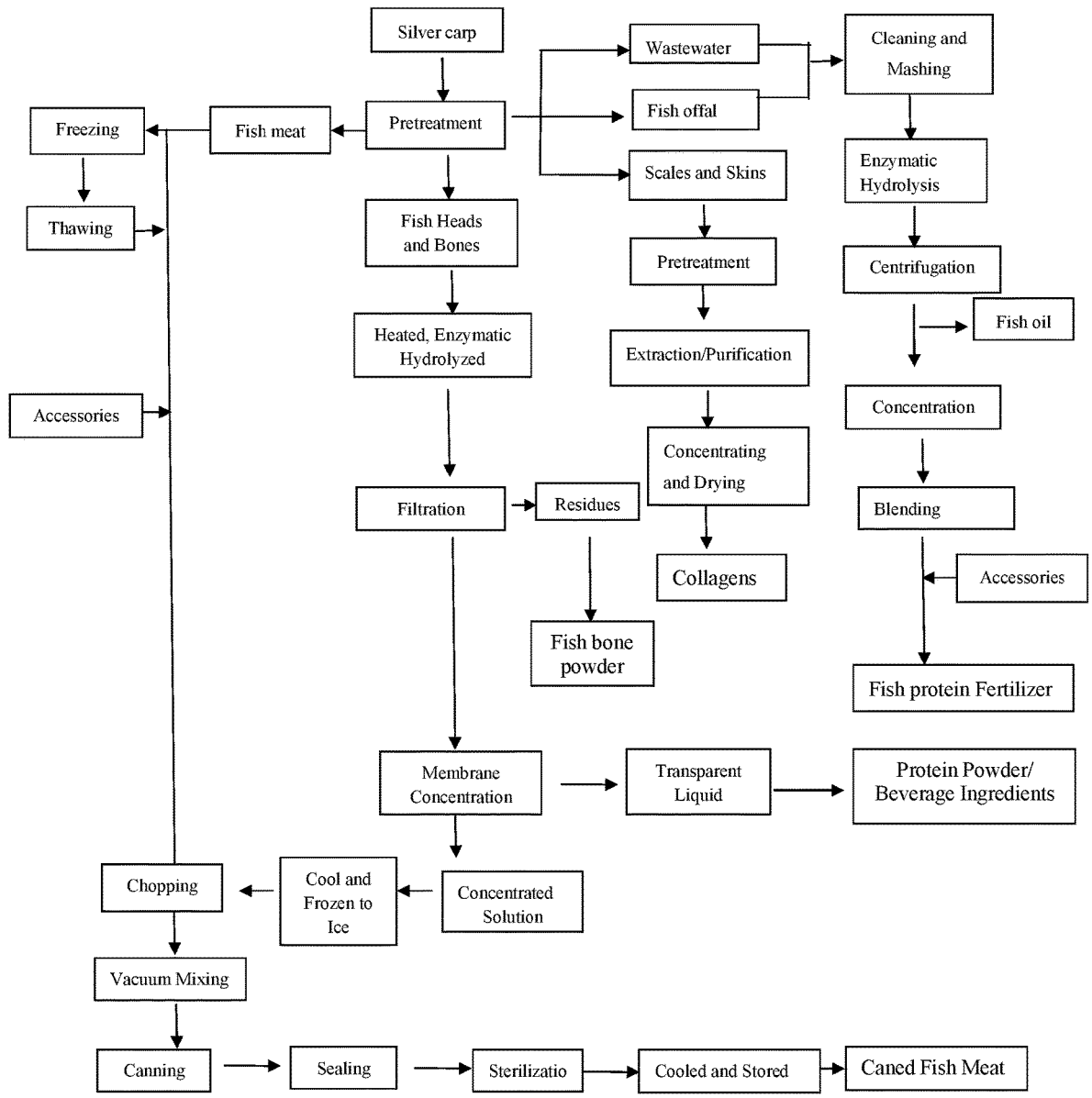

METHOD OF ECOLOGICAL UTILIZATION OF SILVER CARP

RELATED APPLICATIONS

This application claims the benefit of priority of Chinese Application No. 201710891591.X filed on Sep. 27, 2017 entitled A METHOD OF ECOLOGICAL UTILIZATION OF SILVER CARP. The contents of which are incorporated by reference as if fully set forth herein in their entirety.

FIELD OF THE INVENTION

The present invention involves the field of freshwater fish processing technology, especially the method of ecological utilization of silver carp.

BACKGROUND OF THE INVENTION

Silver carp is one of the largest freshwater fish in the world, but the price of silver carp is very low because of the large amount of spines, which to some extent restrict the market value of silver carp.

According to Chinese medicine, silver carp has a lot of health benefits such as to regulate the spleen and stomach, warm the stomach, moisturize the skin and so on. From nutrition analyses, the silver carp skin and scales are rich in collagen, which can be used in functional products for anti-aging and strengthening the body.

In addition, the silver carp is rich in eicosapantaenoic acid (EPA) and decosahexenoic acid (DHA), and contains all the amino acids and elements that human body needs. The composition and content of the essential amino acid in silver carp are very similar to meat. The content of connective tissue in silver carp is small and it is easy to digest. The biological titer of silver carp is very high, which plays a significant role in mental development, reducing cholesterol, reducing blood viscosity and preventing cardiovascular and cerebrovascular disease. The content of taurine in the muscle of silver carp is 68 mg/100 g and taurine plays an important role in the development of nervous system of fetuses and infants. It can also promote the development of the brain, protect the retina and improve the function of the immune system.

The percentage of edible part of silver fish is 260 g/500 g, which contains around protein 21.5%, fat 5.5%, ash 1.4%, calcium 0.3‰ and iron 0.014‰. The trace element content is very rich. The silver carp contains omega-3 fatty acid components that inhibit the spread of cancer cells, so long-term consumption of silver carp (freshwater fish) is of great help in the prevention of cancer. Silver carp (freshwater fish) muscle has good gel formation ability as well, and is an ideal raw material for processing surimi and kamaboko products.

In the 1960s, in order to control the flood of aquatic phytoplankton and algae in the waters, grass carp, followed by silver carp and herring were introduced into the United States. These fish, as pond cleaners, achieved some effects. However, Asian carps, because of their strong survivability and lack of natural enemies, soon spread into the Mississippi River and the Illinois River Basin, and then into the northern part. The traces of Asian carps were also found in Lake Michigan, they further threatened Great Lakes, the junction of the United States and Canada. They also threatened the drinking water sources of about 30 million residents in the United States and Canada. The Asian carps have become one of the significant environmental problems that the US federal and local governments concerned about. Among the Asian carps, including herring, grass carp, bighead carp, silver carp and other carp species, silver carp accounts for 70%.

The US Department of Agriculture has spent more than $18 billion to try to intercept Asian carps further into the Great Lakes region, but the prospect is not optimistic. In the 1990s, the Mississippi River made several floods, therefore, the Asian carps traced Mississippi River to the north, their "Asian Carp Brothers" (even include goldfish and koi) also became "illegal immigrants". Due to the lack of natural enemies, these rapid grow carps have become the local water overlord. In order to eliminate the Asian carps, US Illinois researchers and environmentalists started to put "insecticide" into the river (a total length of 10 km) near Lake Michigan to maintain the ecological balance, but it didn't achieve any effect. In 2017, the US Army Corps of Engineers announced that it had intended to invest $270 million to eliminate the flooded Asian carps by means of establishing dams, river roads, and even grid installations.

In order to solve the problem of the spread of Asian Carps, the United States Michigan Natural Resources Department rewarded 1 million dollars to an effective control plan. The Americans do not like freshwater fish, they don't know how to cook to remove the fishy smell and they dislike fish with numerous spines. Some Americans say that the Asian carps taste good, if we can make a nutritious product, tasty and easy-to-eat, it will be beneficial to solve the ecological problems caused by freshwater fish.

During the processing of Asian carps, a large number of waste product is produced. Fish heads, fish bones, fish offal and residual fish meat account for 40%-60% of the total weight of fish. If these processed wastes cannot be effectively handled, it will not only cause environmental problems, but also lead to a big loss of protein resources.

At present, the degree of comprehensive utilization of freshwater fish offal in China is not high, the general utilizations include: (1) extraction of crude fish oil as feed oil; (2) fish feed produced by microbial fermentation or acid hydrolysis; (3) fishmeal made by drying and smashing. The development and utilization of fish bones are mainly concentrated in three aspects: (1) the preparation of snack food and spices; (2) the preparation of calcium products; (3) fish bone collagen and polypeptide prepared by enzymatic hydrolysis combined with other materialized preparations.

In recent years, with the population growth, the shortage of food resources and the pressure of environmental protection, there is a need to use the existing resources effectively to improve the comprehensive utilization of fish. Therefore, the development and utilization of freshwater fish are becoming more and more important, attracting scholars in food, biology, chemical industry and other fields.

With the development of food science and the progress of technology of aquatic processing industry, the demand for increasing the added value of processed wastes is becoming higher and higher. Therefore, there is a need for the comprehensive utilization of freshwater fish (silver carp) by ecological methods, to use a closed system to enable freshwater fish (sliver carp) meat to be effectively used, including its processed wastes. It is of great practical significance that the ecological methods do not produce environmental wastes, meet the requirements of environmental protection and realize its economic value. It is an object of the present invention to achieve methods and systems that provide an efficient solution to this problem.

SUMMARY OF THE INVENTION

It is an object of the present invention to provide a method for ecological utilization of freshwater fish, especially silver carps.

The technical scheme is as follows:

The fish heads, and bones were heated and enzymatic hydrolyzed by enzymes, the residues of the filtration were prepared for fish bone powder. The filtration membrane was used to reduce the volume of the filtrate to 50% of fish surimi and then the filtrate was frozen to ice. The frozen part can be added to fish surimi. The transparent part from membrane filtration was used to produce protein powder or ingredients for beverages. Fish offal can be used to produce protein liquid fertilizer. Fish scales and skins can be used to produce collagen.

Further, the pretreatment of silver carps includes decapitating, eviscerating and fish sealing. The pretreatment involves separating the fish into 3 parts, rinsing with water below 10° C., draining and sparing.

Further, the specific steps of processing fish heads, and fish bones are as follows:

Step 1: Heating enzymatic hydrolysis: The pretreated fish heads and fish bones were heated and undergo enzymatic hydrolysis, whereby water was added to adjust the solid-liquid ratio, 1%-10% protease was added at a specific pH at 50° C. for enzymatic hydrolysis;

Step 2: Filtration: The hydrolyzed solution from step 1 was filtered to get the filtrate and filter residues, the filtered residues were processed into fish bone powder;

Step 3: Membrane concentration: The filtrate in step 2 was subjected to membrane concentration to obtain both the turbid and transparent part. The volume of the turbid solution was reduced to 50% of the fish surimi to prepare the canned product;

Step 4: Cooling down: The concentrated solution was cooled to room temperature;

Step 5: Freezing: The concentrated solution was put into freezer for freezing;

Step 6: Add to the chopped mix: The ice made from the concentrated solution was added to the fish paste of surimi and chopped together.

A membrane concentration apparatus was used for membrane concentration.

The steps for applying the silver carp meat to make the fish surimi cans are as follows:

Step 1: Chopping: The prepared fish meat, the auxiliary material and the ice concentrate obtained from hydrolysis were mixed, chopped or processed the meat emulsion without granule in the grinding machine;

Step 2: Vacuum mixing: The chopped mixture from Step 1 was vacuum mixed for 60 minutes on vacuum mixture machine;

Step 3: Canning: The fish pastes were canned by the quantitative vacuum filling machine;

Step 4: Sealing: The canned fish products were sealed with a can-sealing machine;

Step 5: Sterilization of products: Sterilization at 105-121° C. for 30-100 minutes to obtain canned fish products.

Further, the canned fish was cooled and stored. The accessories of the step 1 was: edible salt 1%-5%, white sugar 2%-10%, glucose 0.5%-3%, white pepper 0.1%-0.5%, white vinegar 0.5%-3%, cooking wine 1%-5%, potato starch 3%-15%, soybean separated protein 2%-20%, complex phosphate≤0.1%, β-cyclodextrin≤0.1%, blending oil 0.5%-5%, ice made of fish bone concentrate 50%.

Further, the steps for the utilization of fish offal to produce protein liquid fertilizer are as follows:

Step 1: Cleaning and mashing: The silver carp offal was cleaned and crushed by the tissue crusher;

Step 2: Enzyme hydrolysis: Rinsing water from [0016] was added to adjust the solid-liquid ratio, then 0.0%-4% protease was added at about 50° C. for enzymatic hydrolysis;

Step 3: Centrifugation: The hydrolyzed solution of the fish offal was centrifuged to obtain the upper free oil and the lower emulsion;

Step 4: Filtration: The lower emulsion was filtered, and the residues were processed together with the residues obtained by processing the fish heads and the fish bones to the fish bone meal;

Step 5: Concentration: The filtered fish offal solution was concentrated;

Step 6: Blending: The additives or adjutants were added into the concentrated solution according to the recipe of protein liquid fertilizer, prepared with the filter residue to produce fish protein fertilizer.

Further, fish oil can be obtained from Step 3 and the residues can be recovered from the filtering step.

Further, the steps for the utilization of fish scales and skins to produce collagen are as follows:

(1) Extraction of Fish Scale Collagen:

Step 1: Pretreatment: The fish scales were washed, degreased and decolorized if necessary;

Step 2: Extraction: The scales were macerated in hydrochloric acid at pH 4-5 for decalcification until the scales became soft and transparent. Then the scales were washed and heated at 60-70° C. for 2-3 h for 2-5 times until the scales were completely extracted;

Step 3: Concentration: The fish scale collagen was concentrated;

Step 4: Drying: The fish scale collagen was dried until the water content<15%.

(2) Extraction of Fish Skin Collagen:

Step 1: Pretreatment: The scales and meat on the surface of fish skin were removed and washed. The processed skin was soaked in NaOH solution to remove the hetero-protein and soaked in detergent to remove the fat;

Step 2: Extraction: The fish skin was soaked in HAC solution and filtered with single layer gauze;

Step 3: Purification: The pH of the filtrate was adjusted to ≤7.0 with the utilization of NaOH solution. The processed filtrate was set overnight and crushed with a glass rod and spoon, then centrifuged in a centrifuge tube. The HAC solution was added to stir with the processed filtrate in a cool bathing (psychrolusia) until completely dissolved. The dissolved solution was transferred into the dialysis bags by syringe. The dialysis bags were put into a large beaker filled with distilled water and then put onto a magnetic stirrer to dialyze for 3 days. The water was changed 7-8 times per day.

Step 4: Finished product: The gelatinous collagen in the dialysis bags was took out and cut into slices of about 1 mm thickness. The gel slices were freeze dried or tiled into aluminum foil bags, sealed and frozen.

Further, the silver carp can be replaced by carp, grass carp, herring and bighead carp, as the methods of the present invention are also applicable to these species of fish.

The present invention has the following beneficial effects:

The invention adopts the method of ecological utilization, which makes the silver carp meat used effectively, including its processed wastes. The process is a closed cycle process so that no pollutants or wastes are discharged during the processing. The scope of the present invention is not limited to the silver carp, including carp, grass carp, bighead carp and other freshwater fish. The invention utilized three technical routes to maximize the use of fish meat, fish heads, fish bones and fish offal, especially the application of the concentrated liquid made of fish heads and fish bones to the canned fish surimi pastes, which saves a natural cost.

BRIEF DESCRIPTION OF THE DRAWINGS

FIG. 1 is a flow diagram of the steps of the present invention.

DETAILED DESCRIPTION OF THE INVENTION

The invention will now be further described with reference to the accompanying drawings:

Example 1: Silver Carp is Used as the Object to Prepare Fresh Silver Carp

Pretreatment: The pretreatment of silver carps includes decapitating, eviscerating and fish sealing. Separated the fish into 3 parts, rinsed with water below 10° C., drained and spared;

Meat separation: The fish meat was separated, the skin and spines were removed by meat grinder;

Freezing and thawing: The separated meat was frozen in freezer and taken out for thawing if necessary;

Heating enzymatic hydrolysis: Water was added to adjust the solid-liquid ratio, 1%-10% protease was added at the specific pH, 50° C. for enzymatic hydrolysis;

Filtration: The hydrolyzed solution from step 1 was filtered to get the filtrate and filter residues, the filtered residues were processed into fish bone powder;

Membrane concentration: The filtrate in step 2 was subjected to membrane concentration to obtain both the turbid and transparent part. The volume of the turbid solution was reduced to 50% of the fish surimi to prepare the canned product;

Cooling down: The concentrated solution was cooled to room temperature;

Freezing: The concentrated solution was put into freezer for freezing. The ice made from the concentrated solution was added to the can of the fish luncheon paste;

Chopping: The prepared fish meat, the auxiliary material and the ice concentrate obtained from hydrolysis were mixed, chop them or process the meat emulsion without granule in the grinding machine;

Vacuum mixing: The chopped mixture from Step 1 was vacuum mixed for 60 minutes on vacuum mixture machine;

Canning: The fish pastes were canned by the quantitative vacuum filling machine;

Sealing: The canned fish products were sealed with a can-sealing machine;

Sterilization of products: Sterilization at 105-121° C. for 30-100 minutes to obtain canned fish products;

Cooling down: The sterilized cans were removed and cooled to room temperature;

Storage: Sealed cans can be stored at room temperature;

Cleaning and mashing: The silver carp offal was cleaned and crushed by the tissue crusher;

Enzyme hydrolysis: Water was added to adjust the solid-liquid ratio, then 0.0%-4% protease was added at about 50° C. for enzymatic hydrolysis;

Centrifugation: The hydrolyzed solution of the fish offal was centrifuged to obtain the upper free oil and the lower emulsion;

Filtration: The lower emulsion was filtered, and the residues were processed together with the residues obtained by processing the fish heads and the fish bones to the fish bone meal;

Concentration: The filtered fish offal solution was concentrated;

Blending: The additives or adjutants were added into the concentrated solution according to the recipe of protein liquid fertilizer, prepared with the filter residue to produce fish protein fertilizer.

The steps for the utilization of fish scales to produce collagen are as follows:

(1) Extraction of Fish Scale Collagen:

Pretreatment: The fish scales were washed, degreased and decolorized if necessary;

Extraction: The scales were macerated in hydrochloric acid at pH 4-5 for decalcification until the scales became soft and transparent. Then the scales were washed and heated at 60-70° C. for 2-3 h for 2-5 times until the scales were completely extracted;

Concentration: The fish scale collagen was concentrated;

Drying: The fish scale collagen was dried until the water content<15%.

(2) Extraction of Fish Skin Collagen:

Pretreatment: The scales and meat on the surface of fish skin were removed and washed. The processed skin was soaked in NaOH solution to remove the heteroprotein and soaked in detergent to remove the fat;

Extraction: The fish skin was soaked in HAC solution and filtered with single layer gauze;

Purification: The pH of the filtrate was adjusted to ≤7.0 with the utilization of NaOH solution. The processed filtrate was set overnight and crushed with glass rod and spoon, then centrifuged in a centrifuge tube. The HAC solution was added to stir with the processed filtrate in psychrolusia until completely dissolved. The dissolved solution was transferred into the dialysis bags by syringe. The dialysis bags were put into a large beaker filled with distilled water and then put onto a magnetic stirrer to dialyze for 3 days. The water was changed 7-8 times per day.

Finished product: The gelatinous collagen in the dialysis bags was took out and cut into slices of about 1 mm thickness. The gel slices were freeze dried or tiled into aluminum foil bags, sealed and froze.

Example 2: Silver Carp is Used as the Object to Prepare Fresh Silver Carp

Pretreatment: The pretreatment of silver carps includes decapitating, eviscerating and fish sealing. Separated the parts into 3, rinsed with water below 10° C., drained and spared;

Meat separation: The fish meat was separated, the skin and spines were removed by meat grinder;

Freezing and thawing: The separated meat was frozen in freezer and taken out for thawing if necessary;

Heating enzymatic hydrolysis: Water was added to adjust the solid-liquid ratio, 1%-10% protease was added at the specific pH, 50° C. for enzymatic hydrolysis;

Filtration: The hydrolyzed solution from step 1 was filtered to get the filtrate and filter residues, the filtered residues were processed into fish bone powder;

Membrane concentration: The filtrate in step 2 was subjected to membrane concentration to obtain both the turbid and transparent part. The volume of the turbid solution was reduced to 50% of the fish surimi to prepare the canned product;

Cooling down: The concentrated solution was cooled to room temperature;

Freezing: The concentrated solution was put into freezer for freezing. The ice made from the concentrated solution was added to the can of the fish luncheon paste;

Chopping: The prepared fish meat, the auxiliary material and the ice concentrate obtained from hydrolysis were mixed, chop them or process the meat emulsion without granule in the grinding machine;

Vacuum mixing: The chopped mixture from Step 1 was vacuum mixed for 60 minutes on vacuum mixture machine;

Canning: The fish pastes were canned by the quantitative vacuum filling machine;

Sealing: The canned fish products were sealed with a can-sealing machine;

Sterilization of products: Sterilization at 105-121° C. for 30-100 minutes to obtain canned fish products;

Cooling down: The sterilized cans were removed and cooled to room temperature;

Storage: Sealed cans can be stored at room temperature;

Cleaning and mashing: The silver carp offal was cleaned and crushed by the tissue crusher;

Enzyme hydrolysis: Water was added to adjust the solid-liquid ratio, then 0.0%-4% protease was added at about 50° C. for enzymatic hydrolysis;

Centrifugation: The hydrolyzed solution of the fish offal was centrifuged to obtain the upper free oil and the lower emulsion;

Filtration: The lower emulsion was filtered, and the residues were processed together with the residues obtained by processing the fish heads and the fish bones to the fish bone meal;

Concentration: The filtered fish offal solution was concentrated;

Blending: The additives or adjustants were added into the concentrated solution according to the recipe of protein liquid fertilizer, prepared with the filter residue to produce fish protein fertilizer.

The steps for the utilization of fish scales to produce collagen are as follows:

(1) Extraction of Fish Scale Collagen:

Pretreatment: The fish scales were washed, degreased and decolorized if necessary;

Extraction: The scales were macerated in hydrochloric acid at pH 4-5 for decalcification until the scales became soft and transparent. Then the scales were washed and heated at 60-70° C. for 2-3 h for 2-5 times until the scales were completely extracted;

Concentration: The fish scale collagen was concentrated;

Drying: The fish scale collagen was dried until the water content<15%.

(2) Extraction of Fish Skin Collagen:

Pretreatment: The scales and meat on the surface of fish skin were removed and washed. The processed skin was soaked in NaOH solution to remove the heteroprotein and soaked in detergent to remove the fat;

Extraction: The fish skin was soaked in HAC solution and filtered with single layer gauze;

Purification: The pH of the filtrate was adjusted to ≤7.0 with the utilization of NaOH solution. The processed filtrate was set overnight and crushed with glass rod and spoon, then centrifuged in a centrifuge tube. The HAC solution was added to stir with the processed filtrate in psychrolusia until completely dissolved. The dissolved solution was transferred into the dialysis bags by syringe. The dialysis bags were put into a large beaker filled with distilled water and then put onto a magnetic stirrer to dialyze for 3 days. The water was changed 7-8 times per day.

Finished product: The gelatinous collagen in the dialysis bags was took out and cut into slices of about 1 mm thickness. The gel slices were freeze dried or tiled into aluminum foil bags, sealed and froze.

The accessories were added when the fish was chopped. The accessories were as follows: edible salt 1%-5%, white sugar 2%-10%, glucose 0.5%-3%, white pepper 0.1%-0.5%, white vinegar 0.5%-3%, cooking wine 1%-5%, potato starch 3%-15%, soybean separated protein 2%-20%, complex phosphate≤0.1%, β-cyclodextrin≤0.1%, blending oil 0.5%-5%, ice made of fish bone concentrate 50%.

In Example 1, the accessories were as follows: edible salt 1%, white sugar 2%, glucose 0.5%, white pepper 0.1%, white vinegar 0.5%, cooking wine 1%, potato starch 3%, soybean separated protein 2%, complex phosphate≤0.1%, β-cyclodextrin≤0.1%, blending oil 0.5%, ice made of fish bone concentrate 50%.

In Example 2, the accessories were as follows: edible salt 5%, white sugar 10%, glucose 3%, white pepper 0.5%, white vinegar 3%, cooking wine 5%, potato starch 15%, soybean separated protein 20%, complex phosphate≤0.1%, β-cyclodextrin≤0.1%, blending oil 5%, ice made of fish bone concentrate 50%.

As mentioned above, it is only a specific way of implementation of the invention, but the scope of protection of the invention is not limited to this. Changes and substitutions that anyone familiar with the technology in this field can easily thought of should be contained in the scope of the invention protection.

What is claimed is:

1. A method for the ecological utilization of one or more fish, the method comprising:
pretreating one or more fish by separating the one or more fish into three parts including a) meat, b) head and bones, and c) scales and viscera, and rinsing the one or more fish with water below 10° C.;
heating the head and bones of the one or more fish;
hydrolyzing the head and bones of the one or more fish via protease;
filtering the head and bones of the one or more fish via a filtration membrane to reduce the volume of the one or more fish, whereby upon filtration, the one or more fish is separated into a filtrate and filter residues;
processing the filter residues into fish bone powder;
processing the filtrate, whereby the filtrate is used for a canned fish product; and
freezing the filtrate to ice,
wherein the fish is selected from a group consisting of silver carp, carp, grass carp, herring, or bighead carp.

2. The method of claim 1, wherein the filtrate is transparent, and further comprising processing the transparent part of filtrate to produce protein powder or ingredients for beverages.

3. The method of claim 1, further comprising preparing the filtrate residues for fish bone powder.

4. The method of claim 1, wherein the scales are used to produce collagen.

5. The method of claim 1, wherein the filtrate is processed canned surimi.

6. The method of claim 1, wherein the pretreatment of fish further comprises decapitating, eviscerating and sealing the one or more fish.

7. The method of claim 1, wherein heating the heads and bones of the one or more fish comprises heating to enzymatically hydrolyze the heads and bones of the one or more fish, by adding water to adjust the solid-liquid ratio, and by adding 1%-10% protease at 50° C. to produce enzymatic hydrolysis;

filtering the head and bones of the one or more fish comprises subjecting the one or more fish to a membrane filtration to obtain both a turbid part that cannot pass through the membrane and a transparent part that can pass through the membrane, wherein the volume of the turbid part is reduced to 50% to prepare the canned surimi product, and wherein the turbid part is cooled to room temperature; and freezing the filtrate comprises adding ice to the filtrate, such that the ice and filtrate form a concentrated solution is added to the canned fish product.

8. The method of claim 1, further comprising applying the meat from the one or more fish to make the fish luncheon pastes.

9. The method of claim 8, wherein the fish luncheon pastes are made by:
   a) chopping the one or more fish;
   b) vacuum mixing the chopped one or more fish for 60 minutes on vacuum mixture machine;
   c) canning the fish pastes via a quantitative vacuum filling machine;
   d) sealing the canned fish products with a can-sealing machine; and
   e) sterilizing the canned fish products at 105-121° C. for 30-100 minutes to obtain canned fish products.

10. The method of claim 9, wherein chopping the one or more fish involves the prepared fish meat, the auxiliary material and the ice concentrate obtained from hydrolysis, and mixing the fish meat with the auxiliary material and the ice concentrate and chopping or processing the material.

11. The method of claim 8, wherein the cooling and storage of the canned fish includes using edible salt 1%-5%, white sugar 2%-10%, glucose 0.5%-3%, white pepper 0.1%-0.5%, white vinegar 0.5%-3%, cooking wine 1%-5%, potato starch 3%-15%, soybean separated protein 2%-20%, complex phosphate ≤0.1%, β-cyclodextrin ≤0.1%, blending oil 0.5%-5%, ice made of fish bone concentrate 50%.

12. The method of claim 1, further comprising utilizing the scales and viscera fish offal to produce protein liquid fertilizer.

13. The method of claim 1, further comprising utilizing the scales to make collagen.

14. The method of claim 13, wherein the collagen is made by:
   (1) pretreating the fish scales by washing, degreasing and/or decolorizing;
   (2) extracting the scales by macerating in hydrochloric acid at pH 4-5 for decalcification, until the scales become soft and transparent, then washing the scales 2-5 times, at 60°-70° C for 2-3 hours;
   (3) concentrating the fish scale collagen;
   (4) drying the fish scale collagen to a water content of less than 15%.

* * * * *